United States Patent [19]

Khair et al.

[11] Patent Number: 5,425,710
[45] Date of Patent: Jun. 20, 1995

[54] COATED SLEEVE FOR WRAPPING DILATATION CATHETER BALLOONS

[75] Inventors: Alexander K. Khair, San Diego; Darryl A. Anderson, Riverside, both of Calif.

[73] Assignee: Medtronic, Inc., Minneapolis, Minn.

[21] Appl. No.: 142,779

[22] Filed: Oct. 26, 1993

[51] Int. Cl.$^6$ .............................................. A61M 25/00
[52] U.S. Cl. ...................................... 604/96; 606/194
[58] Field of Search ....................... 604/96, 95, 51, 52, 604/99, 104; 606/191, 194; 128/662.06, 772, DIG. 21

[56] References Cited

U.S. PATENT DOCUMENTS

| | | |
|---|---|---|
| 4,287,892 | 9/1981 | Schiff . |
| 4,540,404 | 9/1985 | Wolvek . |
| 4,710,181 | 12/1987 | Fuqua . |
| 4,738,666 | 4/1988 | Fuqua . |
| 4,762,129 | 9/1988 | Bonzel . |
| 4,917,097 | 4/1990 | Proudian et al. . |
| 4,952,357 | 8/1990 | Euteneuer . |
| 5,015,230 | 5/1991 | Martin et al. . |
| 5,032,113 | 7/1991 | Burns . |
| 5,040,548 | 8/1991 | Yock . |
| 5,053,007 | 10/1991 | Euteneuer . |
| 5,061,273 | 10/1991 | Yock . |
| 5,066,298 | 11/1991 | Hess . |
| 5,067,491 | 11/1991 | Taylor, II et al. . |
| 5,116,318 | 5/1992 | Hillstead . |
| 5,221,260 | 6/1993 | Burns et al. . |
| 5,334,154 | 8/1994 | Samson et al. . |
| 5,352,236 | 10/1994 | Jung et al. . |

OTHER PUBLICATIONS

Pyle, Jeff "Low Cost Coating Stands Up to Altervative Fuels" *Machine Design*, May 14, 1993, pp. 77–79.

*Primary Examiner*—C. Fred Rosenbaum
*Assistant Examiner*—Perry E. Van Over
*Attorney, Agent, or Firm*—Dianne M. F. Plunkett; Harold R. Patton

[57] ABSTRACT

A hollow, cylindrical protector for a dilatation catheter balloon. The disclosed protector is made from silicone tubing having a coating on at least an inner surface thereof for enhancing the lubricity of the protector and thus facilitating easy installation of the protector over a dilatation catheter's balloon. In this way, the risk of damage to the balloon resulting from protector installation is reduced. In the disclosed embodiment, the inner surface of a silicone balloon protector is coated via vacuum deposition or the like with parylene. The parylene-coated protector is then slid over a deflated and wrapped dilatation catheter balloon. The catheter is then subjected to elevated temperatures for the purposes of heat-setting. The elevated temperatures cause the silicone protector to be reduced in diameter, further reducing the balloon's profile. Also, the compression and heating causes the balloon material to heat-set, increasing the reliability of symmetrical deflation and re-wrap of the balloon.

6 Claims, 3 Drawing Sheets

COATED SLEEVE FOR WRAPPING DILATATION CATHETER BALLOONS

FIELD OF THE INVENTION

This invention relates to the field of angioplasty, and more particularly to a balloon protector of a dilatation balloon catheter.

BACKGROUND OF THE INVENTION

Angioplasty has become widely accepted as an efficient and effective method for opening stenoses in the coronary arteries and in other parts of the vascular system. The most widely used form of angioplasty makes use of a dilatation catheter which has an inflatable balloon at its distal end. Using fluoroscopy, the physician guides the catheter through the vascular system until the balloon is positioned across the stenosis. The balloon is then inflated by supplying a fluid under pressure through an inflation lumen to the balloon. The inflation of the balloon causes stretching of the artery and pressing of the lesion into the artery wall to reestablish acceptable blood flow through the artery.

One important characteristic of a dilatation catheter used for angioplasty is its profile, i.e., the outer diameter of the distal end portion of the balloon. Considerable effort has been spent in developing low-profile dilatation balloon catheters by minimizing the dimensions of the core or inner tube which extends through the balloon to its distal end, and by reducing wall thicknesses, to the extent possible, of the balloon itself.

Another important consideration is the outer diameter of the catheter in its deflated condition. This outer diameter affects the ease and ability of the dilatation catheter to pass through a guide catheter and through the coronary arteries leading to the stenosis to be opened.

In order to reduce the outer diameter of the balloon catheter in its deflated condition, it is common to fold or wrap the flaps of the deflated balloon. When inflation fluid is applied to the deflated balloon, it causes the balloon flaps to unwrap so that the balloon can inflate to its fully inflated condition.

In the prior art, it has been common to use a balloon protector in conjunction with a balloon dilatation catheter. A balloon protector serves at least two important functions. First, it protects the balloon and distal tip of the catheter from possible damage during shipping. Second, the balloon protector keeps the balloon tightly wrapped in its deflated condition to minimize the outer diameter of the balloon in its deflated state.

A balloon protector is typically applied to the distal end portion of the catheter prior to sterilization of the catheter. The sterilization process can involve exposing the catheter, with the balloon protector in place, to an elevated temperature for a period of time.

With certain balloon materials, the sterilization process will advantageously cause the balloon to be heat set in the folded or wrapped configuration in which it is held by the balloon protector. As a result, when the balloon protector is later removed, the balloon remains in this tightly wrapped or folded configuration. The heat setting of a balloon has the further advantage that when the balloon is inflated and then deflated, as it may be several times during an angioplasty procedure, the application of negative pressure during deflation will cause the balloon to return to its tightly wrapped heat set configuration. This greatly facilitates the removal of the catheter after the procedure has been performed.

Various types and configurations of balloon protectors have been shown in the prior art, for example, in U.S. Pat. Nos. 4,738,666 and 4,710,181 to Fuqua, in U.S. Pat. No. 5,053,007 to Euteneuer, in U.S. Pat. No. 5,066,298 to Hess, in U.S. Pat. No. 5,116,318 to Hillstead, and in U.S. Pat. No. 4,540,404 to Wolvek.

The above-noted Fuqua '666 and '181 patents propose a catheter protector comprising a hollow cylindrical sheath. The Fuqua sheath covers the entire length of the catheter, and is removed by pulling it off of the proximal end of the catheter. Fuqua also proposes providing perforations in the sheath for facilitating its removal. A similar arrangement is proposed in the above-referenced Wolvek '404 patent, in which a sheath is slidably disposed over a substantial section of a catheter body, covering the balloon disposed at the distal end of the catheter body. The sheath and catheter assembly are advanced into the patient's vascular system until the distal balloon end is positioned in the area to be dilated. The sheath is long enough that its proximal end remains exposed outside of the patient, such that the sheath may be withdrawn along the catheter body until the balloon is uncovered. Then, the dilatation procedure can be performed.

The above-noted Euteneuer '007 patent proposes a compression protector employing an inner sleeve applied over a deflated balloon, an outer sleeve applied over the inner sleeve, and a compression housing for compressing the outer sleeve radially in on the inner sleeve, thus compressing the inner sleeve radially in on the balloon. With the balloon thus compressed within the Euteneuer '007 protector, the catheter is then sterilized at an elevated temperature. The inner and outer sleeves are formed of materials which exhibit heat-shrink qualities such that the heat treatment causes the balloon to be further compressed to a smaller outer diameter. The Euteneuer '007 protector is removed just prior to introduction of the catheter into the patient, with the balloon retaining its compressed form as a result of the heat treatment.

The above-noted Hess '298 patent proposes protecting a catheter's balloon by wrapping the balloon with tape in an overlapping fashion. In a manner similar to that proposed in the Euteneuer '007 reference, the Hess '298 balloon is subjected to heat treatment after being wrapped, in order to further compress the balloon and affect a heat-setting of the balloon in its compressed condition.

In the above-referenced Hillstead '318 patent, there is proposed an elastic sleeve for covering the balloon of a catheter used for placement and expansion of an expandable intraluminal stent. The Hillstead sleeve is provided to facilitate withdrawal of the balloon from the intraluminal stent.

As catheter distal sections, including catheter balloons, have become smaller, thinner, and more fragile, it has become increasingly difficult to apply a balloon protector which does not damage the catheter or the balloon and yet wraps the balloon as tightly as possible. This is particularly true with balloon protectors which take the form of hollow cylindrical tubing, which can be quite difficult to slide over a wrapped balloon.

To overcome such difficulties, it has been proposed in the prior art to use a low-friction material, such as Teflon ™ or the like, for a hollow cylindrical balloon protector, such that the difficulty in sliding the protector over the wrapped balloon is minimized. Notwithstanding such proposals, however, there is perceived by the inventor to be a continuing need for improved balloon protectors for dilatation balloon catheters.

SUMMARY OF THE INVENTION

Accordingly, the present invention is directed to an improved balloon protector for covering and protecting the balloon of a dilatation catheter.

In particular, and in accordance with one aspect of the present invention, a dilatation balloon protector is provided for which the risk of damage to the balloon during installation of the protector is reduced.

In accordance with another feature of the present invention, a dilatation balloon protector is provided which exhibits heat-shrink characteristics, such that upon installation of the balloon and heat sterilization, the wrapped balloon is compressed and maintained in an even more tightly wrapped configuration.

The foregoing and other aspects of the present invention are realized through provision of a silicone, hollow cylindrical balloon protector having a thin coating on at least the inner surface thereof, such that the lubricity of the inner surface is enhanced. In a preferred embodiment of the invention, the balloon protector is coated with parylene, facilitating the easy installation of the protector over a wrapped dilatation balloon.

After installation of the protector, the balloon and protector are subjected to elevated temperatures for the purposes of heat-setting. This causes the silicone protector to shrink to decreased diameter, further compressing the balloon in its wrapped configuration and minimizing the balloon's profile. The rubbery characteristics of the silicone tube will maintain the pressure evenly on the balloon after it cools. The heat also causes a heat-setting of the balloon material, such that the balloon tends to maintain its tightly wrapped configuration even after the protector is removed prior to use of the catheter in a procedure. The heat setting further tends to enhance the reliability of symmetrical wrap and rewrap of the balloon during the procedure.

BRIEF DESCRIPTION OF THE DRAWINGS

The foregoing and other features of the present invention will be best appreciated with reference to the following detailed description of a specific embodiment of the invention, when read in conjunction with the accompanying drawings, wherein:

FIG. 5 is an enlarged cross-sectional end view of the balloon protector from FIG. 3.

DETAILED DESCRIPTION OF A SPECIFIC EMBODIMENT OF THE INVENTION

Figure 1:
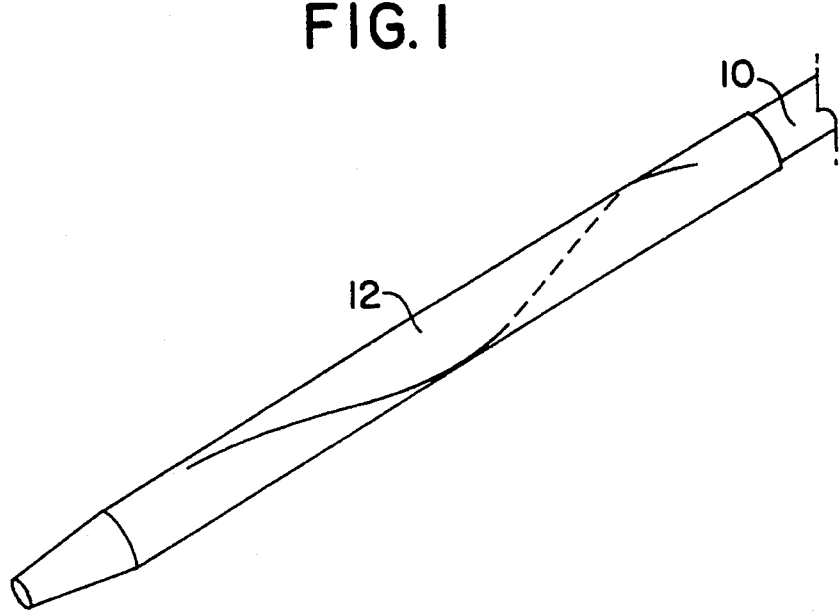
FIG. 1 is an enlarged perspective view of the distal end of a dilatation catheter and balloon in accordance with one embodiment of the present invention, shown with the balloon in a deflated, wrapped condition.

Referring to FIG. 1, there is shown an enlarged perspective view of a distal end portion of a balloon dilatation catheter 10 including a dilatation balloon 12 shown in a deflated, wrapped condition.

Those of ordinary skill in the art will appreciate that there are presently a wide assortment of dilatation balloon catheters known and commercially-available from numerous sources. For example, there are catheters of the so-called "over-the-wire" type and of the so-called "rapid exchange" type. Examples of the latter type are discussed in U.S. Pat. Nos. 5,040,548 and 5,061,273 to Yock and in U.S. Pat. No. 4,762,129 to Bonzel (see also Reexamination Certificate No. B1 4,762,129. Moreover, there are catheters having spiral-wrapped balloons, as discussed for example in U.S. Pat. No. 5,015,230 to Martin et al., and catheters having so-called "tri-fold" balloon configurations, as discussed for example in the above-referenced Euteneuer et al. '007 patent.

In accordance with an important feature of the present invention, it is believed that the present invention may be advantageously practiced in conjunction with many or perhaps all of the presently known types of balloon dilatation catheters. Therefore, although a particular type of balloon and catheter configuration may be depicted in the Figures and described herein in some detail, it is to be understood that this is done solely for the purposes of illustrating various aspects and features of the present invention and is not intended to be limiting with respect to the scope of the invention.

In accordance with one embodiment of the present invention, balloon 12 is preferably made of an elastic, biocompatible material such as PE, LLDPE, PET, POC or the like.

Figure 2:
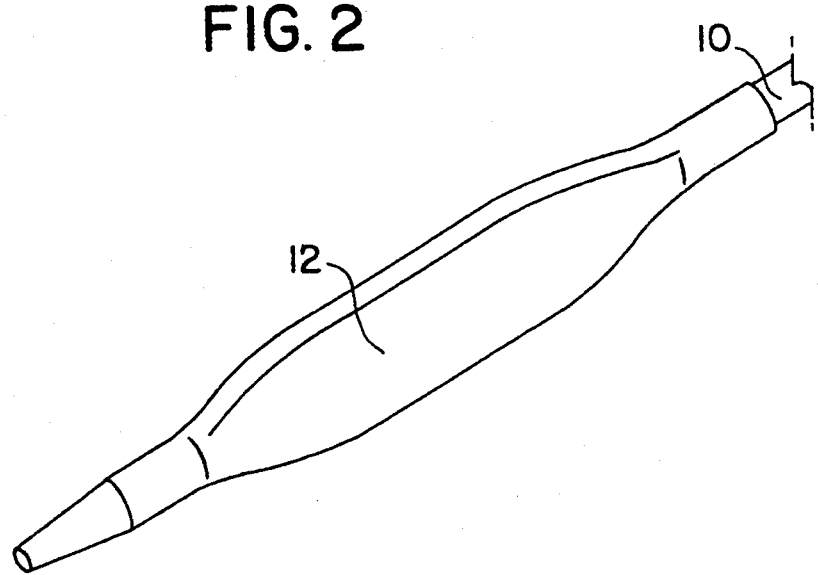
FIG. 2 is an enlarged perspective view of the catheter and balloon from FIG. 1, shown with the balloon in an inflated condition.

In FIG. 2, there is shown an enlarged perspective view of catheter 10 and balloon 12, with balloon 12 now in an inflated condition and thus having a substantially enlarged outer diameter as compared with the profile of balloon 12 in the deflated, wrapped condition depicted in FIG. 1.

As will be appreciated by those of ordinary skill in the art, and as previously discussed, a protective sleeve or sheath is often disposed around balloon 12 prior to sterilization of the catheter or at some other phase of preparation of the catheter, so that balloon 12 is maintained in a tightly wrapped and compressed configuration until just prior to use of the catheter in an angioplasty procedure.

As discussed in the above-referenced Euteneuer '007 patent, a protective sleeve or sheath may be provided which exhibits heat-shrinking characteristics, such that when the balloon and protective covering are subjected to heat during a sterilization process, the protective covering shrinks to further compress and heat-set balloon in a tightly-wrapped configuration. Such heat-setting is believed to be advantageous because it tends to cause balloon 12 to reliably deflate to a symmetrical low profile during a dilatation procedure.

Figure 3:
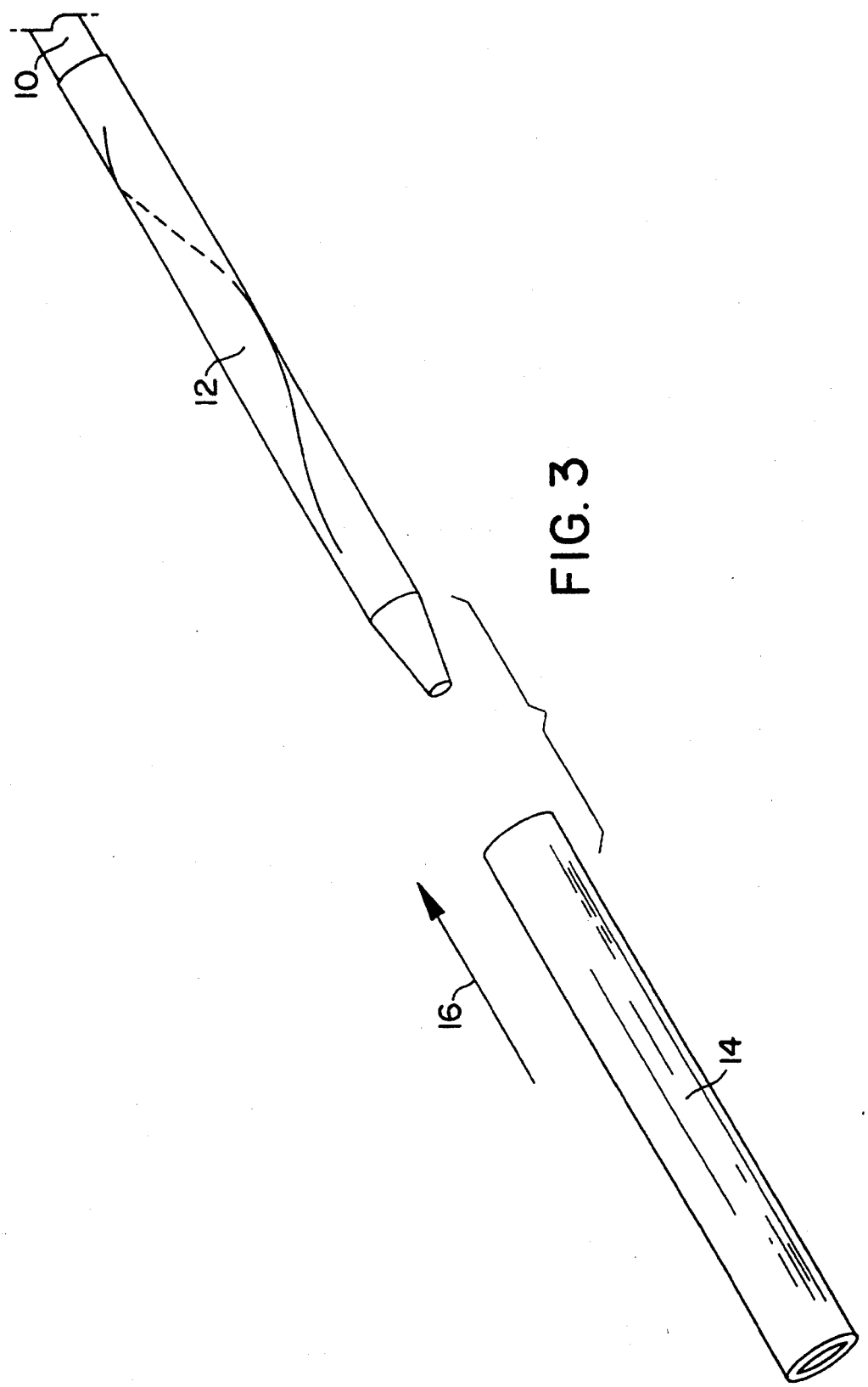
FIG. 3 is an enlarged perspective view of a hollow cylindrical balloon protector in accordance with one embodiment of the invention, shown in the process of being installed over the balloon of FIG. 1.

In FIG. 3, there is shown an enlarged perspective view of a hollow cylindrical balloon protector 14 in the process of being installed around balloon 12 which has been wrapped in accordance with any one of various known techniques. Installation of protector 14 involves sliding protector 14 across balloon 12 from the distal end, i.e., in the direction of arrow 16 in FIG. 3.

In accordance with one aspect of the presently disclosed embodiment of the invention, balloon protector 14 is made of a material which exhibits heat-shrink characteristics. In the presently preferred embodiment of the invention, balloon protector 14 is preferably made of silicone tubing which, by its nature, shrinks in diameter when exposed to elevated temperatures. Thus, if balloon protector 14 has an internal diameter somewhat larger than the diameter of balloon 12 in the deflated, wrapped condition of FIG. 1, protector 14 may be slid over balloon 12 and then heat-set to further compress balloon 12 in its deflated, wrapped condition. The heat-setting also has an "ironing" effect on balloon 12, resulting in a better wrap and re-wrap of the balloon.

Those of ordinary skill in the art will appreciate, however, that silicone is generally "sticky" with respect to materials out of which balloon 12 is made. Such stickiness makes it difficult for protector 14 to be slid over balloon 12. In accordance with an important aspect of the present invention, therefore, protector 14 is provided with a coating, on at least the inner surface thereof, of a material which enhances the lubricity of protector 14 for the purposes of sliding protector 14 over a deflated, wrapped dilatation balloon. In particular, and in accordance with the presently preferred embodiment of the invention, at least the inner surface of protector 14 is coated with parylene, which is known to lower the surface energy attraction of rubber and thermoplastic materials.

Parylene is a polymer developed by Union Carbide Corporation, and was first used to coat electronic and computer components such as high-density disk drives and the like. In such applications, parylene is believed to be useful in excluding minute dust, fibers, smoke particles, and other microscopic contaminants.

It has also been proposed in the prior art that parylene may be useful in enhancing the ability of certain elastomeric automobile components (e.g., seals, gaskets, grommets, and the like) to resist chemical attack. See, e.g., Pyle, Jeff, "Low Cost Coating Stands Up to Alternative Fuels", *Machine Design*, May 14, 1993, pp. 77–79.

Parylene is vacuum-deposited on a substrate at room temperature, which allows the polymer to form with equal, time-controlled densities on all types of surfaces. The penetrating nature of vacuum-deposition produces an inert, non-reactive, pin-hole free coating that provides environmental barrier protection, chemical resistance, and mechanical and dielectric strength. Coating-layer thicknesses can range from one-tenth $\mu$m to several $\mu$m.

Figure 4:
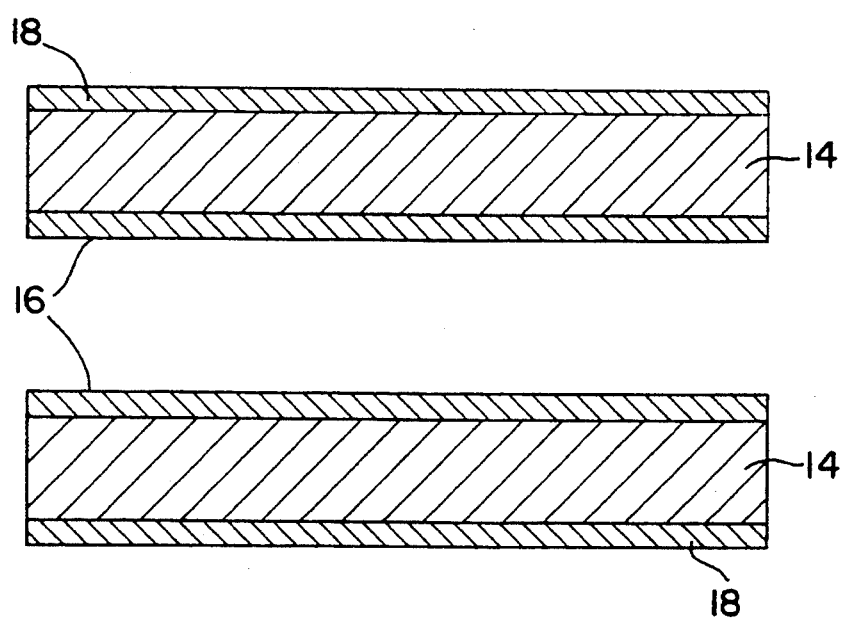
FIG. 4 is an enlarged cross-sectional longitudinal view of the balloon protector from FIG. 3.

Referring to FIGS. 4 and 5, there shown cross-sectional longitudinal views, of protector 14 in accordance with the presently disclosed embodiment of the invention. As shown in FIGS. 4 and 5, protector 14 is provided with a thin, smooth, and slippery coating of parylene on both its inner surface and its outer surface. In particular, a parylene coating 16 is provided on the inner surface of hollow cylindrical balloon protector 14, and a parylene coating 18 is provided on the outer surface of protector 14. The parylene coating, and in particular the parylene coating 16 on the inner surface of protector 14, such that protector 14 may be more easily slid over balloon 12. Thus, the risk of damage to balloon 12 as a result of protector installation is reduced. Heat sterilization of balloon 12 with protector 14 installed causes protector 14 to shrink in diameter, further compressing balloon 12 into its wrapped configuration.

Those of ordinary skill in the art will appreciate that different diameters of silicone tubing will be needed for different balloon types and sizes. It has been the inventors' experimental experience that 0.0940 cm $\times$ 0.216 cm (0.037- $\times$ 0.085-inch) parylene-coated silicone tubing is effective to wrap and heat-set 2.5-mm size balloons. Heat-setting has been performed at 37° C. for 10 minutes in a dry heat station.

From the foregoing detailed description of a specific embodiment of the invention, it should be apparent that an improved balloon protector for a dilatation balloon has been disclosed. Although a specific embodiment of the invention has been described herein in some detail, it is to be understood that this has been done for the purposes of illustration only, and is not intended to be limiting with respect to the scope of the invention. It is contemplated that various substitutions, alterations, and/or modifications, including but not limited to those specifically discussed herein, may be made to the disclosed embodiment without departing from the spirit and scope of the present invention as defined in the appended claims, which follow.

What is claimed is:

1. A removable balloon protector for a dilatation catheter, which is removed prior to catheter insertion, comprising:
    a hollow, cylindrical tube made of silicon, having inner and outer surfaces; and
    a parylene coating on at least said inner surface of said tube increasing the lubricity of said inner surface.

2. A balloon protector in accordance with claim 1, wherein said parylene is vacuum deposited.

3. A method of preparing a dilatation balloon catheter having an inflatable balloon at a distal end thereof, comprising the steps of:
    wrapping said balloon such that said balloon defines a substantially circular cross-section of a first diameter;
    coating, with parylene, at least an inner surface of a hollow cylindrical silicone protector having a second diameter larger than said first diameter;
    sliding said protector over said wrapped balloon;
    exposing said balloon and protector to elevated temperatures, such that said protector shrinks to have a third diameter, smaller than said first diameter.

4. A method in accordance with claim 3, wherein said step of coating comprises vacuum depositing parylene on at least an inner surface of said protector.

5. A catheter system comprising:
    a catheter having a proximal end and a distal end;
    a balloon affixed to the distal end; and
    a removable balloon protector comprising a hollow, cylindrical tube made of silicone, having inner and outer surfaces, a parylene coating on at least said inner surface of said tube, said coating increasing the lubricity of said inner surface, said balloon disposed within said tube.

6. A catheter system according to claim 5, wherein said parylene is vacuum deposited.

* * * * *